US00PP12046P2

(12) United States Plant Patent
Zaiger et al.

(10) Patent No.: US PP12,046 P2
(45) Date of Patent: Aug. 14, 2001

(54) PEACH TREE NAMED 'SUGAR TIME'

(76) Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 0 days.

(21) Appl. No.: 09/473,824

(22) Filed: Dec. 28, 1999

(51) Int. Cl.[7] ..... A01H 5/00
(52) U.S. Cl. ..... Plt./197
(58) Field of Search ..... Plt./197

*Primary Examiner*—Bruce R. Campell
*Assistant Examiner*—June Hwu

(57) ABSTRACT

A new and distinct variety of peach tree (*Prunus persica*), which has the following unique combination of desirable features that are outstanding in a new variety. The features of the tree and its fruit are characterized with the tree budded on Nemaguard Rootstock (non-patented), grown on Hanford sandy loam soil with Storie Index rating 95, in USDA Hardiness Zone 9, near Modesto, Calif., and with standard commercial cultural fruit growing practices, such as, pruning, thinning, spraying, irrigation and fertilization:

1. Early maturity of large size, yellow flesh fruit.
2. Fruit having a mild, sweet, sub-acid flavor with excellent eating quality.
3. Fruit having firm flesh with good handling and shipping quality.
4. heavy and regular production of fruit.
5. Fruit having a high degree of attractive red skin color.
6. The tree having a vigorous, upright growth habit.

1 Drawing Sheet

BACKGROUND OF THE VARIETY

In the field of plant genetics we conduct an extensive and continuing plant-breeding program including the origination and asexual reproduction of orchard trees, of which peaches, nectarines, apricots, cherries, plums and interspecifics are exemplary. It is against this background of our activities that the present variety of peach tree was originated and asexually reproduced by us in our experimental orchard located near Modesto, Stanislaus County, Calif.

PRIOR VARIETIES

The existing varieties of peach and nectarine trees, which are known to us, and mentioned herein, are May Crest Peach (U.S. Plant Pat. No. 4,064), Ventura Peach (non-patented), Spring Crest Peach (non-patented), Fayette Peach (non-patented), May Grand Nectarine (U.S. Plant Pat. No. 2,794) and Sweet Gem Peach (U.S. Plant Pat. No. 7,952).

ORGIN OF THE VARIETY

The present new variety of peach tree (*Prunus persica*) was developed by us in our experimental orchard located near Modesto, Calif., as a first generation cross, made in 1989, between two selected seedlings with field identification numbers 45GA424 (non-patented) and 7.5HB605 (non-patented). The maternal parent (45GA424) was selected for future use in our breeding program and originated from a cross of two seedling selections. One seedling originated from a cross of Fayette Peach (non-patented) with a nectarine of unknown parentage. The other selected seedling originated from open pollinated seed of May Grand Nectarine (U.S. Plant Pat. No. 2,794). The paternal parent (7.5HB605) originated from a cross of a selected seedling with May Crest Peach (U.S. Plant Pat. No. 4,064). The selected seedling originated from a cross between Ventura Peach (non-patented) and Spring Crest Peach (non-patented). We planted and grew a large group of these first generation seedlings, on their own root, under close observation, during which time we recognized the outstanding fruit characteristics described within and selected the present variety for asexual reproduction and commercialization.

ASEXUAL REPRODUCTION OF THE VARIETY

Asexual reproduction of the new and distinct variety of peach tree was by budding to Nemaguard rootstock (non-patented), the standard rootstock for peaches in California, as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

The new and distinct variety of peach tree is of large size, vigorous upright growth and a regular and productive bearer of large, yellow flesh, clingstone fruit with excellent flavor and eating quality. The fruit is further characterized with ripening in the early maturity season, having a high degree of attractive red skin color and having firm flesh, good handling and shipping quality. In comparison to the yellow flesh, mild, sweet, sub-acid, Sweet Gem Peach (U.S. Plant Pat. No. 7,952), the new variety is approximately 16 days later in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, age 8 years, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large. Pruned to 12 to 14 feet in height at maturity for economical harvesting of fruit.

*Vigor.*—Vigorous. Tree reaching 6 to 8 feet in height and 5 to 6 feet in width during first growing season. During first dormant season the tree is pruned to 3 to 4 feet in height and primary scaffolds are selected.

*Growth.*—Upright. The center branches are removed, forming a vase shape, to increase air movement and sunlight throughout the tree to enhance fruit color and new fruit wood growth.

*Productivity.*—Productive. Fruit set is two or more times the amount needed for normal crop load and fruit must be thinned and spaced to develop desirable market size fruit.

*Bearer.*—Regular. Has set adequate crop load for 6 consecutive years.

*Form.*—Pruned to vase shaped.

*Density.*—Medium dense. Removal of center branches by pruning is necessary for air movement and sunlight to penetrate center of tree.

*Hardiness.*—Tree grown in USDA Hardiness Zone 9. Winter chilling requirement is approximately 800 hours below 45° F.

Trunk:

*Size.*—Large. Measured 26 inches in circumference at 15 inches above ground on 8 year old tree.

*Texture.*—Medium shaggy, varies slightly with age of tree.

*Color.*—Mouse gray to beaver brown (5-E-3) to (5-F-4).

Branches:

*Size.*—Medium. Average measurement of 14 inches in circumference at 43 inches above ground. Varies with age of tree.

*Texture.*—Smooth to medium rough. Varies with age of growth.

*Lenticels.*—Medium number. Medium to large size, average 18 within 4 square inch surface, counted 36 inches above ground. Average length 3/16 inch. Average width 3/32 inch. Color — golden wheat to Chinese yellow (4-B-5) to (4-B-7).

*Color.*—Light tan to light brown (6-C-8) to (6-D-8), varies with age of growth.

Leaves:

*Size.*—Large. Average length 7½ inches. Average width 1⅞ inches.

*Form.*—Lanceolate.

*Margin.*—Crenate.

*Thickness.*—Medium.

*Surface.*—Upper surface — smooth. Lower surface — relatively smooth, slightly ridged in venation areas.

*Petiole.*—Medium. Average length ½ inch. Medium thickness, grooved. Color — light green to grayish green (29-D-4) to (29-D-6).

*Glands.*—Reniform. Number varies from 1 to 5. Average number 2. Small to medium in size. Average length 3/64 inch. Average width 1/32 inch. Positioned on base of leaf blade and upper portion of petiole. Color varies from spring green to yellowish green (30-C-6) to (30-C-8). Secretion of sticky fluid collects dust and impurities from air and changes to darker color.

*Color.*—Upper surface — green to dark green (27-E-8) to (27-F-8). Lower surface — grayish green to green 29-D-6) to (29-D-8). Leaf color varies slightly with fertility of soil.

Flower buds:

*Size.*—Medium to large. Average length 37/64 inch. Average width 25/64 inch. Three days before bloom.

*Form.*—Plump.

*Pubescence.*—Pubescent.

*Color.*—Light pink to pastel pink (11-A-3) to (11-A-5).

*Hardiness.*—Hardy in all stone fruit growing areas of California.

Flowers:

*Flower development.*—Normally one flower bud on each side of leaf bud on previous years new growth. Perigynous, complete, single pistil, multiple stamens, five petals and sepals alternately positioned.

*Size.*—Large, showy. Average height 1 inch. Average diameter 1½ inches.

*Petal.*—Number — 5, alternately arranged to sepals. Nearly orbicular, narrower at point of attachment, edges vary from smooth to slightly scalloped. Average length 29/32 inch. Average width ⅜ inch.

*Sepals.*—Number—5, alternately arranged to petals. Size — medium. Average length 15/64 inch. Average width 11/64 inch. Color — upper surface brownish orange (6-C-6), fades with age of flower. Lower surface — dull red (11-C-5), fades as flower ages.

*Aroma.*—Very slight.

*Stamens.*—Number varies from 20 to 37. Average filament length 31/64 inch. Filament color — white to pale pink (12-A-1) to (12-A-3), fades with age of flower. Anther color — butter cup yellow to light orange (4-A-7) to (5-A-7).

*Pistil.*—Number — one. Average length 21/32 inch. Color — white (1-A-1). Pubescence.

*Pollen.*—Present, self-fertile. Color — yellow to sunflower yellow (4-A-6) to (4-A-7).

*Blooming period.*—Date of First Bloom Mar. 1, 1999. Date of Last Bloom Mar. 9, 1999. Varies slightly with climatic conditions.

*Color.*—Pink to light pink (11-A-4) to (11-A-3). Color fades with age of flowers.

Fruit:

*Maturity when described.*—Shipping ripe.

*Date of first picking.*—Jun. 25, 1999.

*Date of last picking.*—Jul. 2, 1999. Varies slightly with climatic conditions.

*Size.*—Average diameter axially 2⅝ inches. Average transversely in suture plane 2⅞ inches. Average weight 178 grams. Average weight varies slightly with fertility of the soil, amount of thinning and climatic conditions.

*Form.*—Nearly globose, slightly flattened at both apex and base.

*Suture.*—Nearly smooth, only very slight depression, extends from base to apex.

*Ventral surface.*—Rounded.
*Apex.*—Slightly retuse.
*Base.*—Retuse.
*Cavity.*—Rounded, slightly elongated in suture plane. Average depth ⅜ inch. Average breadth ⅞ inch.

Skin:
*Thickness.*—Medium.
*Texture.*—Medium, tenacious to the flesh.
*Down.*—Moderate amount, medium length.
*Tendency to crack.*—None.
*Color.*—Mellow yellow to chrome yellow (5-A-6) to (5-A-8) ground color. Overspread with deep red to Bordeaux red (11-C-8) to (11-D-8), with small areas of ground color showing, leaving a dappled to mottled pattern in some of the surface area. Amount and degree of red color varies with amount of the fruit exposed to sunlight.

Stem:
*Size.*—Average length ⅜ to ½ inch. Average diameter 3/32 inch.
*Color.*—Olive yellow to grayish yellow (3-C-8) to (3-D-8).

Flesh:
*Ripens.*—Evenly.
*Texture.*—Firm.
*Fibers.*—Few, small, tender.
*Aroma.*—Slight.
*Amygdalin.*—Undetected.
*Eating quality.*—Excellent.
*Flavor.*—Excellent.
*Juice.*—Moderate, mild, sweet, enhances flavor.
*Brix.*—12.2°.
*Color.*—Butter yellow to sunflower yellow (4-A-5) to (4-A-7). Pit cavity — butter yellow to amber yellow (4-A-5) to (4-B-6).

Stone:
*Type.*—Clingstone.
*Size.*—large. Average length 1½ inches. Average width 1⅛ inches. Average thickness ⅝ inch.
*Form.*—Ovate.
*Base.*—Usually straight, varies from straight to rounded.
*Apex.*—Acuminate.
*Surface.*—Irregularly furrowed toward apex, pitted toward base. Pits vary from round to elongated.
*Sides.*—Unequal, one side larger, extending outward farther from suture plane.
*Ridges.*—Rounded, relatively wide with a few rough surface areas.
*Tendency to split.*—Very slight.
*Color.*—Yolk yellow (4-B-8).

Use: Dessert. Market, local and long distance.

Keeping quality: Good. Fruit stored for 3 weeks at 38° to 42° F. showed no internal breakdown or wooliness.

Shipping quality: Good. Fruit packed and shipped showed minimal bruising of flesh or skin scarring.

Plant disease: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed, during indexing of plant characteristics, with abnormal fungus, bacterial, virus, or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous, upright growth and being a productive and regular bearer of large, yellow flesh, clingstone fruit with excellent flavor and eating quality; the fruit is further characterized by having firm flesh, good packing and storage quality, having an attractive red skin color, and, in comparison to the mild, sweet, sub-acid Sweet Gem Peach (U.S. Plant Pat. No. 7,952), the variety is approximately 16 days later in maturity.

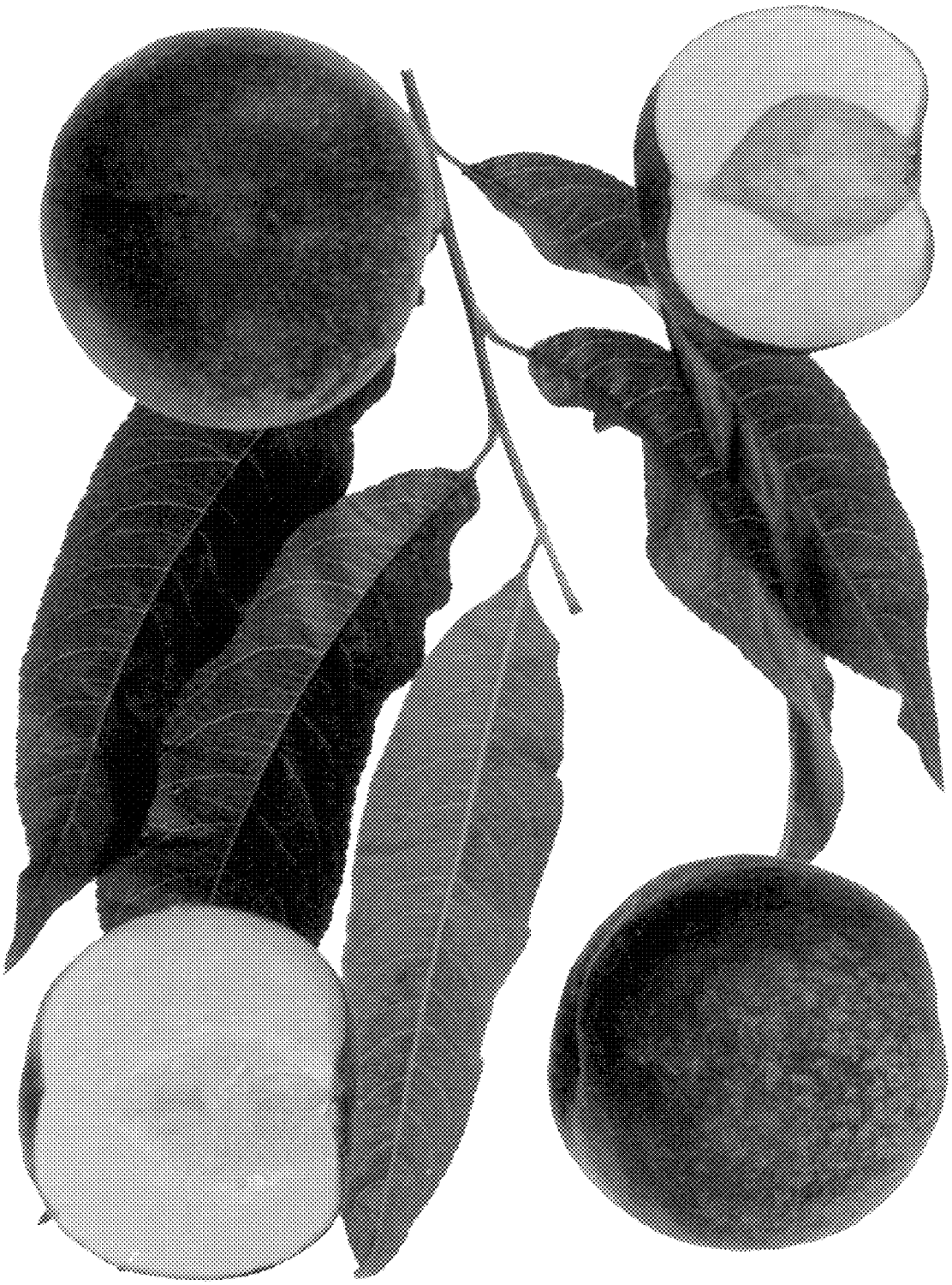

* * * * *